(12) United States Patent
Cruchaga et al.

(10) Patent No.: US 10,105,056 B2
(45) Date of Patent: Oct. 23, 2018

(54) SYSTEM AND METHOD FOR ACQUIRING IMAGES OF VEINS OF A FINGER

(71) Applicant: MORPHO, Issy les Moulineaux (FR)

(72) Inventors: Michel Cruchaga, Issy les Moulineaux (FR); Sylvaine Picard, Issy les Moulineaux (FR)

(73) Assignee: MORPHO, Issy les Moulineaux (FR)

( * ) Notice: Subject to any disclaimer, the term of this patent is extended or adjusted under 35 U.S.C. 154(b) by 216 days.

(21) Appl. No.: 14/878,212

(22) Filed: Oct. 8, 2015

(65) Prior Publication Data
US 2016/0100761 A1 Apr. 14, 2016

(30) Foreign Application Priority Data
Oct. 9, 2014 (FR) ...................................... 14 59666

(51) Int. Cl.
| | | |
|---|---|---|
| *H04N 5/33* | (2006.01) | |
| *A61B 5/00* | (2006.01) | |
| *G06K 9/00* | (2006.01) | |
| *G06K 9/20* | (2006.01) | |
| *H04N 5/225* | (2006.01) | |
| *H04N 7/18* | (2006.01) | |

(52) U.S. Cl.
CPC ........ *A61B 5/0059* (2013.01); *G06K 9/00013* (2013.01); *G06K 9/2027* (2013.01); *H04N 5/2256* (2013.01); *H04N 5/33* (2013.01); *H04N 7/183* (2013.01)

(58) Field of Classification Search
None
See application file for complete search history.

(56) References Cited

U.S. PATENT DOCUMENTS

| | | | | |
|---|---|---|---|---|
| 5,986,271 | A | * 11/1999 | Lazarev | ................. A61B 1/043 |
| | | | | 250/458.1 |
| 2005/0205667 | A1 | 9/2005 | Rowe | |
| 2010/0026453 | A1* | 2/2010 | Yamamoto | .............. G06F 21/32 |
| | | | | 340/5.83 |
| 2014/0016832 | A1* | 1/2014 | Kong | ................... A61B 5/1171 |
| | | | | 382/115 |

(Continued)

FOREIGN PATENT DOCUMENTS

| | | |
|---|---|---|
| CN | 101642372 A | 2/2010 |
| EP | 1610265 A1 | 12/2005 |
| EP | 1830123 A1 | 9/2007 |

OTHER PUBLICATIONS

Mar. 20, 2015 Search Report issued in French Patent Application No. 1459666.

*Primary Examiner* — Janese Duley
(74) *Attorney, Agent, or Firm* — Oliff PLC; R. Brian Drozd

(57) ABSTRACT

A system for acquiring an image of veins of a finger includes a camera designed to acquire an image of said finger when it is passed in front of it, a lighting device designed to illuminate said finger and a control unit for controlling the illumination intensity of said lighting device. Also, at least one system measures the transmission power of said finger upstream of the camera with respect to the passage of said finger towards said camera, said control unit being designed to control the illumination intensity of said lighting device according to the transmission power measured by said measuring system. Additionally, a method for acquiring images of veins of a finger is provided.

8 Claims, 6 Drawing Sheets

(56) References Cited

U.S. PATENT DOCUMENTS

| | | | |
|---|---|---|---|
| 2014/0265920 A1* | 9/2014 | Pederson | H05B 33/0842 |
| | | | 315/294 |
| 2015/0051500 A1* | 2/2015 | Elliott | A61B 5/6898 |
| | | | 600/480 |

* cited by examiner

SYSTEM AND METHOD FOR ACQUIRING IMAGES OF VEINS OF A FINGER

FIELD OF EMBODIMENTS OF THE INVENTION

The present invention relates to a system and a method for acquiring images of veins in a finger.

A system for acquiring images of veins is provided with an illumination device, generally an infrared one, for illuminating the fingers of the person to be authenticated and a camera for collecting the light transmitted by these fingers in order to acquire an image thereof. The acquired image may also be used for the recognition of fingerprints. The absorption of the light by the haemoglobin flowing in the veins of the fingers makes it possible to reveal these veins in the acquired image in a highly effective manner. This illumination by transmission makes it possible to acquire good-quality images of fingers and thus to reveal with precision the venous network of these fingers even in difficult cases of thick fingers or with a dermis that is itself thick. Nevertheless, to do this, it is necessary to adapt the power of the illumination to the transmission power of the fingers. This is because, for a very thick finger or one with a thick dermis, the illumination power must be high whereas, for a thin finger or with a very fine skin, the illumination power must be reduced, in particular in order not to completely saturate the camera and obtain a completely blank image that cannot be used because the venous network does not appear therein.

A finger vein acquisition system according to the invention is of the so-called on-the-fly type, in which the user presents his moving fingers between the illumination device and the camera. Because of this, the time that is allocated for making one or more image acquisitions is then very brief, generally less than two seconds. During this time, apart from the acquisition of images, it is necessary to adjust the lighting power so as to adapt it to the transmission power of the fingers, the image of which is to be acquired.

BACKGROUND

One method of the prior art for making this adjustment of the illumination power is to proceed by servocontrolling this power from the brightness of the images acquired. Thus the illumination power is adjusted firstly to an arbitrary value and an image is required. The brightness of the image is measured and the illumination power is corrected depending on whether this brightness is low or on the contrary too great. A new image is acquired with this new lighting power, its brightness is measured and the power is corrected if necessary, until convergence.

This method is effective but, because it is iterative and thus requires several image acquisitions, it is expensive in terms of time and is therefore scarcely usable for acquisition on the fly.

Another method could also use the exposure measurement devices of cameras but this would require expensive instrumentation around the camera. Moreover, exposure measuring devices may be disturbed by the type of scene to be treated, for example in the case of scenes where the background is completely saturated, or by the movement of the fingers, the region of the image to be exposed correctly then being changeable.

None of these lighting control methods is suited to the acquisition of images of finger veins on the fly.

SUMMARY

The aim of the present invention is therefore to provide a system for acquiring images of finger veins that is suited to acquisition on the fly.

Thus a system for acquiring an image of veins of a finger according to the present invention is of the type that comprises a camera designed to acquire an image of said finger when it is passed in front of it, a lighting device designed to illuminate said finger and a control unit for controlling the intensity of illumination of said lighting device. It is characterised in that it comprises a system for measuring the transmission power of said finger upstream of the camera with respect to the passage of said finger towards said camera, said control unit being designed to control the illumination intensity of said lighting device according to the transmission power measured by said measuring system.

According to another advantageous feature, it is characterised in that said control unit functions in a learning mode for the elaboration and storage of the function linking the illumination intensity of said lighting device to said transmission power.

According to a particular embodiment of the invention, it is characterised in that said control unit receives the image signal from said camera and is designed to complete the adjustment of the illumination intensity of said lighting device by servocontrolling from one or more images acquired by means of said camera.

According to another particular embodiment of the invention, it is characterised in that said camera is designed to deliver an image on a plurality of channels, the first channel being more sensitive than the second, which is itself more sensitive than the third, etc., as far as the last one, said control unit receiving one of said channels and being designed to control the intensity of illumination of said lighting device so that said channel is generally correctly exposed, said acquisition system further comprising a selector controlled by said control unit in order to select the channel among said channels that is best exposed.

According to another particular embodiment of the invention, it is characterised in that said measuring system comprises two photoemitter/receiver pairs, the photoemitter of one being designed to emit at a higher light intensity than the photoemitter of the other.

According to another particular embodiment of the invention, it is characterised in that said or each photoemitter of said measuring system has its light intensity controlled by said control unit.

The present invention also relates to a method for acquiring an image of veins of a finger implemented by means of an acquisition as just described.

BRIEF DESCRIPTION OF THE DRAWINGS

The features of the invention mentioned above, as well as others, will emerge more clearly from a reading of the following description of example embodiments, said description being given in relation to the accompanying drawings, among which.

DETAILED DESCRIPTION OF EMBODIMENTS OF THE INVENTION

Figure 1:
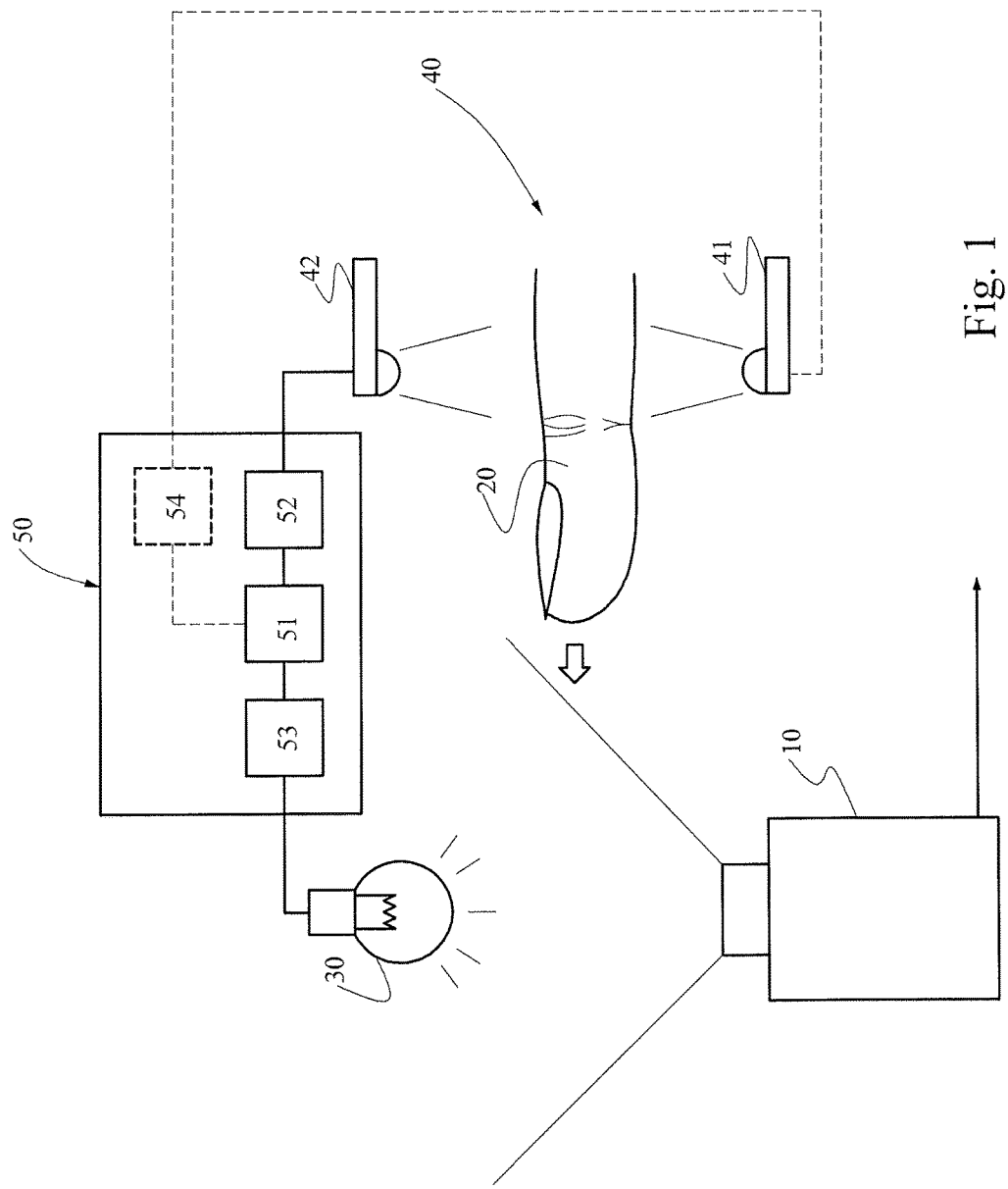
FIG. 1 is a schematic view of a system for acquiring images of veins of a finger according to a first embodiment of the invention.

The system for acquiring images of veins of fingers depicted in FIG. 1 essentially comprises a camera 10 designed to acquire an image of a finger 20 when passing in front of it and being illuminated, by transmission, by means of a lighting device 30 (depicted in the form of a lamp) designed to effect lighting in near infrared light between 750 nm and 1100 nm, for example 850 nm.

The acquisition system of FIG. 1 also comprises a system 40 for measuring the transmission power of a finger 20 that is offered up in front of the camera 10. In the example embodiment depicted, this measuring system comprises a photoemitter 40, such as a light emitting diode or LED, and a photodetector 42 such as a phototransistor or a photodiode. The photoemitter 41 emits light radiation in the near infrared range, for example with wavelengths of between 750 nm and 1100 nm, at a predetermined constant light intensity. It may therefore be a light emitting diode emitting radiation at a wavelength of 860 nm. As for the photodetector 42, it may be a photodiode designed to detect infrared radiations with wavelengths of between 750 nm and 1100 nm. The photoemitter 41 and the photodetector 42 are arranged so that a finger that seeks to be offered up in front of the camera 10 so that the latter acquires an image thereof previously passes between both of them, as depicted in FIG. 1. They are therefore offset laterally upstream, in the direction of passage of the finger 20, with respect to the camera 10 and lighting device 30. The photodetector 42 receives the light from the photoemitter 41 after transmission thereof by the finger 20. Thus the signal delivered by the photodetector 42 represents the light intensity that it receives and therefore the transmission power of the finger 20 for the radiation emitted by the photoemitter 41. If the considered finger is thick or has a thick dermis, the light intensity measured by the photodetector 42 is weak whereas, if it is thin or has a thin dermis, this light intensity is high. The signal delivered by the photodetector 42 is in proportion to the light intensity transmitted by the finger 20.

The acquisition system of FIG. 1 also comprises a control unit 50 that is designed firstly to receive the light intensity signal delivered by the photodetector 42 and secondly to control the illumination intensity of the lighting device 30. Thus, if the light intensity signal delivered by the photodetector 42 represents a low transmitted light intensity (the finger is in this case rather thick or has a thick dermis), the control unit 50 controls the lighting device 30 so that its illumination is rather intense (rather high light intensity). Conversely, if the light intensity signal delivered by the photodetector 42 represents a high transmitted light intensity (the finger is in this case rather thin or has a thin dermis), the control unit 50 controls the lighting device 30 so that its lighting is rather low (rather low light intensity).

Figure 2:
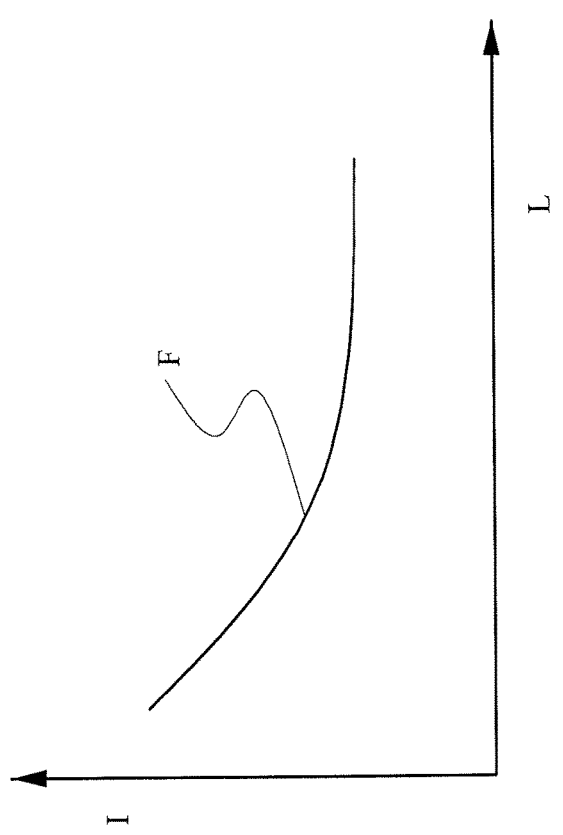
FIG. 2 is a graph showing the function that links the illumination intensity of a lighting device to the light intensity measured by a measuring system of an acquisition system according to the invention.

The function F thus performed by the control unit 50 can be represented by a curve in FIG. 2 showing the intensity of the illumination I of the lighting device 30 according to the amplitude L of the transmitted light intensity signal delivered by the photodetector 42.

In an advantageous embodiment, the control unit 50 functions in a learning mode for producing and storing the function F linking the light intensity of the lighting device 30 to said transmission power of the fingers. Thus, in this learning mode, a plurality of fingers are passed through the measuring system 40 and then in front of the camera 10. For each finger passed, firstly the transmitted light intensity received by the photodetector 42 is measured, and secondly the illumination intensity of the lighting device 30 is sought for a good quality of the image acquired by the camera 10. They are put together in relation to produce and store the function F. After the execution of this learning mode, the control unit 50 is operational.

In a particular embodiment, the control unit 50 comprises a control unit 51, an analogue to digital converter 52 for converting into a digital signal the transmitted light intensity signal delivered by the photodetector 42 and to deliver it to the central unit 51, and a digital to analogue converter 53 for converting the digital control signal delivered by the central unit 51 into an analogue signal for controlling the lighting device 30.

The advantage of the acquisition system of the present invention results from the fact that the illumination intensity of the lighting device 30 is determined sufficiently quickly for the lighting device 30 to be already correctly adjusted at the moment when the finger the image of which is to be acquired is situated in front of the camera 10. This is because the response time of the measuring device 40 and of the control unit 50 is very short, around a few microseconds, must less than the time taken by the finger 20 to pass from the position in the measuring system 40 to the position in front of the camera 10.

Figure 3:
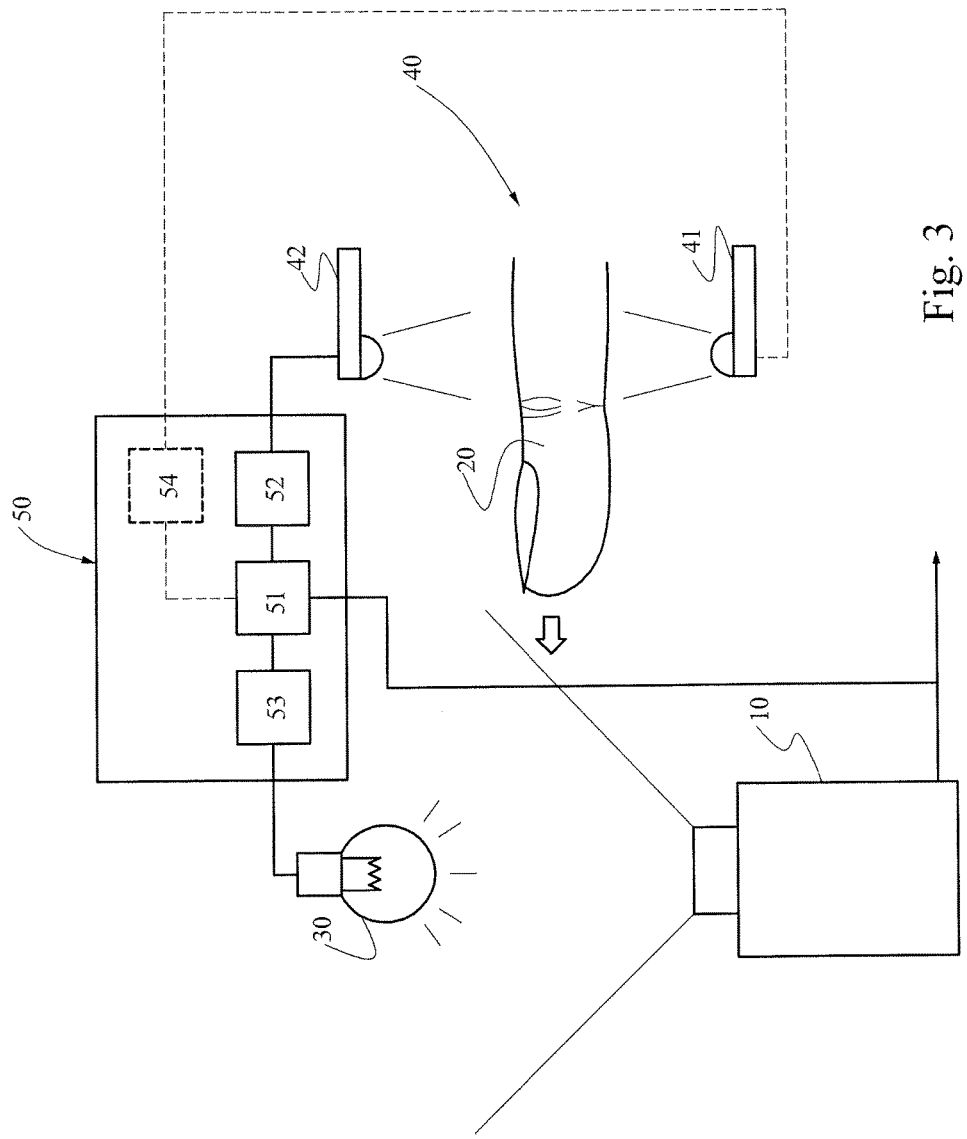
FIG. 3 is a schematic view of a system for acquiring images of veins of a finger according to a second embodiment of the invention.

In another embodiment depicted in FIG. 3, the adjustment of the illumination of the lighting device 30 is initialized by means of the measuring system 40, as just described in relation to FIG. 1, and is then completed by servocontrolling from one or more images acquired by means of the camera 10. In the embodiment depicted, the image signal acquired by the camera 10 is supplied to the central unit 51, which then implements an optimisation process similar to the servocontrol adjustment process of the prior art. Such a process uses for example an image analysis of the histogram type from which an offset is defined and used, by the central unit 51, for adjusting the lighting device 30. The advantage of the use of the measuring system 40 lies in the fact that the number of iterations for acquiring an image of good quality is reduced compared with the acquisition systems of the prior art, because the measuring system 40 makes it possible to initialize the illumination intensity to a value that is very close to the optimum value. Only one or a few iterations are sufficient to complete the adjustment.

The camera 10 may be a monochromatic camera sensitive to infrared radiation. It delivers a luminance signal representing the light emitted by the lighting device 30 and transmitted by the finger 20 when it is in front of it. This is the case in FIGS. 1 and 3.

Figure 4:
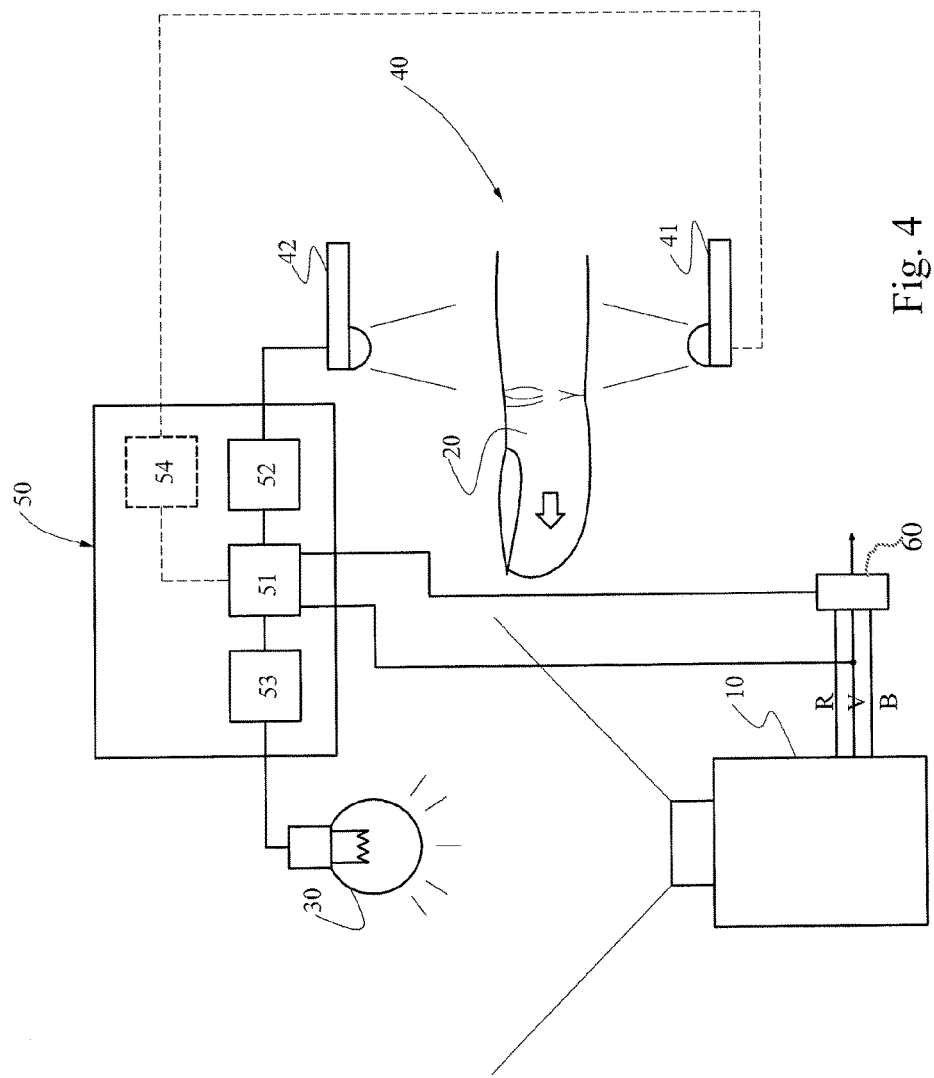
FIG. 4 is a schematic view of a system for acquiring images of veins of a finger according to a third embodiment of the invention.

In another embodiment depicted in FIG. 4, the camera 10 is a camera with several colour channels, for example three colour channels: one green, another red and the other blue. Each channel is sensitive to the infrared radiation emitted by the lighting device 30 (near infrared). However, the gain of each channel is adjusted on the camera so that the first channel is more sensitive than the second channel, which itself is more sensitive than the third, etc., as far as the last. Thus, in case of three channels red, green, blue, one (the red) is more sensitive than the second (the green), itself more sensitive than the third (the blue). The measuring system 40 is designed to control the lighting device 30 so that the image of a particular channel (for example, the green channel) is generally of good quality. In this embodiment, each image issuing from the particular channel is supplied to the central unit 51, which then evaluates the exposure of the obtained image. In addition, the acquisition system depicted comprises a selector 60 that is controlled by the central unit 51 so as to select, as an output signal, the channel that is best exposed among the channels delivered by the camera 10.

The selection operation is implemented as follows: if the image of the particular channel (for example a green channel) is correctly exposed, it is this image of the particular channel that is selected by the selector 60. If it is slightly underexposed, the central unit 51 pilots the selector 60 so that the image of the most sensitive channel (in the example given, the red channel) is selected, and conversely, if it is slightly overexposed, it controls the selector 60 so that the image of a less sensitive channel (in this case the blue) is selected.

Figure 5:
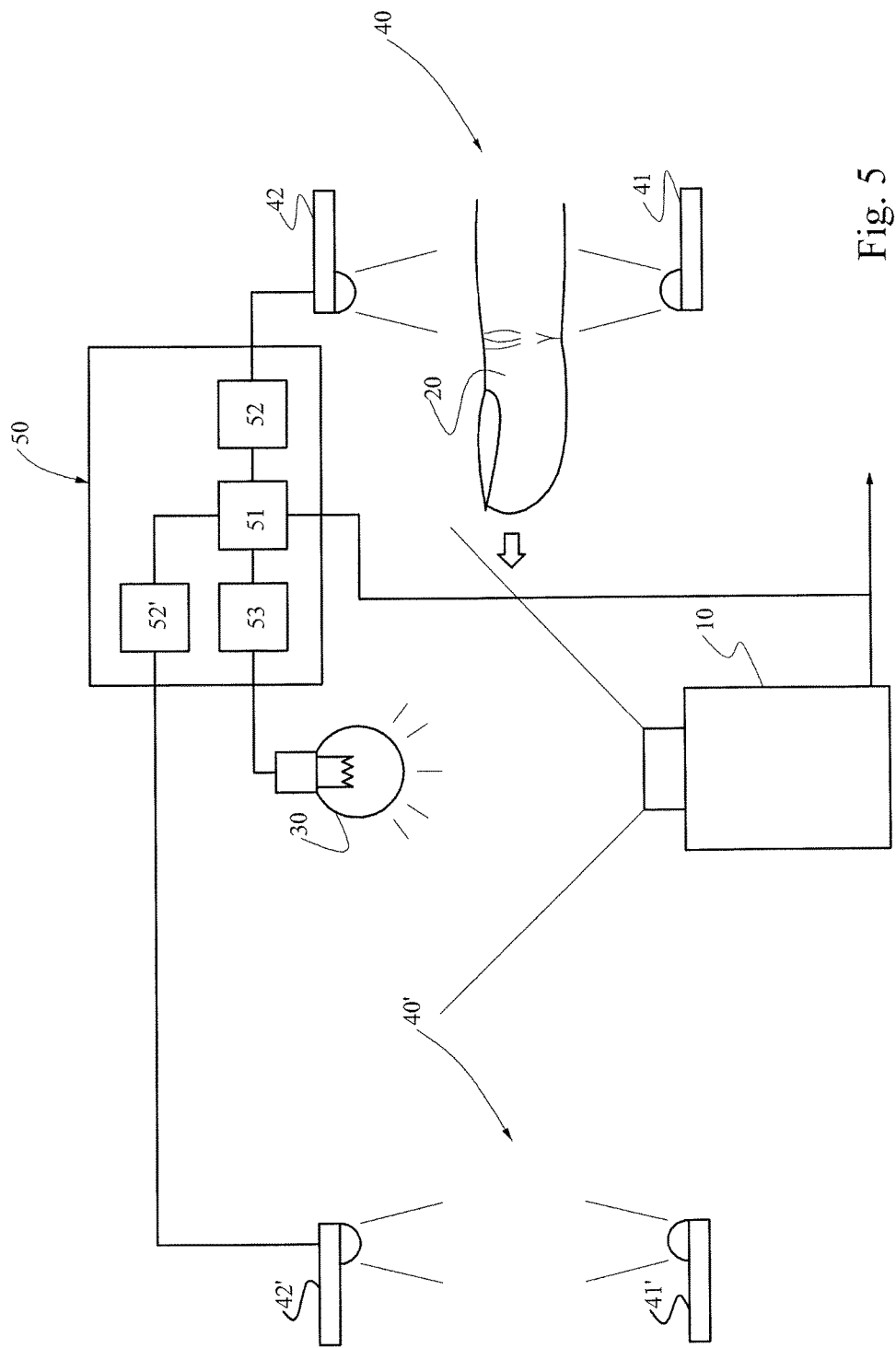
FIG. 5 is a schematic view of a system for acquiring images of veins of a finger according to a fourth embodiment of the invention.

In FIG. 5, the acquisition system comprises two measuring systems 40 and 40', one comprising a photoemitter 41 and a photodetector 42 and the other a photoemitter 41' and a photodetector 42' both identical to those that were described in FIGS. 1 and 3. The photodetector 42' delivers a light intensity signal to an analogue to digital converter 52' connected to the central unit 51. In the embodiment depicted, the photoemitters 41 and 41' emit a constant predetermined light intensity, one (provided for fingers with a rather thick dermis) at a higher light intensity than the other (provided for fingers with a rather thin dermis). The principle is to provide one measuring system for fingers with a thick dermis and the other for fingers with a thin dermis.

Both in FIG. 1 and in FIGS. 3 and 4, broken lines represent optional means 54 for controlling the light intensity of the photoemitter 41. These means 54 consist of a digital to analogue converter 54, the input of which is connected to the central unit 51 and the output of which is connected to the photoemitter 41. For example, the photodetector 42 functions in a small light intensity range. A first measurement is made by the measuring system 40 at a low light intensity emitted by the photoemitter 41. If the finger 20 is thin or has a thin dermis, the photodetector 42 receives sufficient light and can make a measurement with sufficient precision. On the other hand, if the finger is thicker or has a thicker dermis, the photodetector 42 no longer receives sufficient light and cannot correctly make the measurement. Then a second measurement is made with a higher light intensity emitted by the photoemitter 41. Several light intensity levels may thus be provided.

Figure 6A:
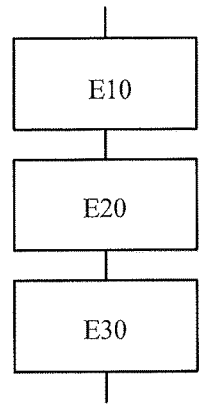
FIGS. 6a to 6d are diagrams illustrating the steps of an acquisition method according to the present invention.

FIG. 6a shows a diagram of a method for acquiring an image of veins of a finger according to the invention. This method is implemented by means of an acquisition system such as those that have been described above in relation to FIGS. 1 to 5. This acquisition system thus comprises a camera 10 designed to acquire an image of a finger 20 when it is passed in front of it and a lighting device 30 for illuminating said finger 20. An acquisition method according to the invention comprises a step E20 of adjusting the illumination intensity of the lighting device 30 and a step E30 of acquisition of said image by said camera 10.

According to the invention, it is characterised in that it further comprises a step E10 of measuring the transmission power of said finger implemented prior to the presentation of said finger in front of the camera 10, said step E20 of adjusting said lighting device 30 consisting of controlling the illumination intensity of said lighting device 30 according to the transmission power measured at the measuring step E10.

Advantageously, the function linking the illumination intensity of said lighting device 30 to said transmission power is obtained by learning.

Figure 6B:
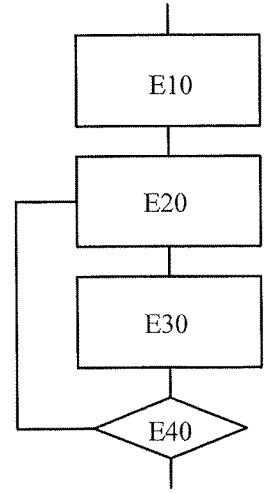

FIG. 6b is a diagram showing another embodiment of an acquisition method according to the invention. Apart from steps E10 to E30 described previously in relation to FIG. 6a, it comprises a step E40 of checking the exposure of the image acquired during said acquisition step E30, a new step E20 of adjusting the intensity of the lighting of said lighting device 30 being carried out if the exposure of said image is judged to be incorrect. This adjustment is at:

an illumination intensity lower than the previous illumination intensity if the exposure of said image is judged to be overexposed at step E40, an illumination intensity higher than the previous illumination intensity if the exposure of said image is judged to be underexposed at step E40.

Figure 6C:
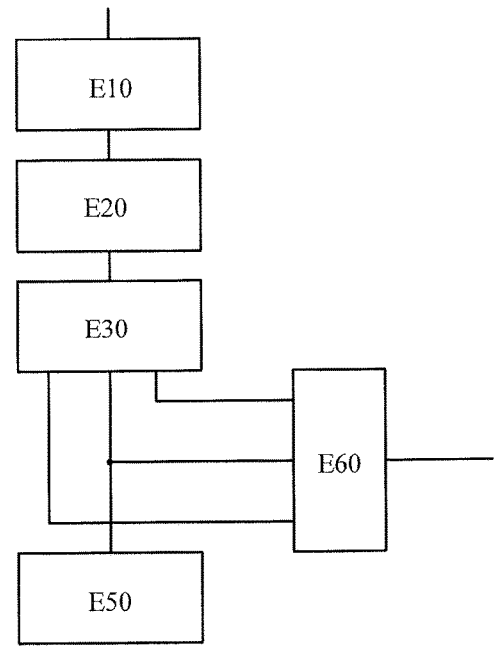
Figure 6D:
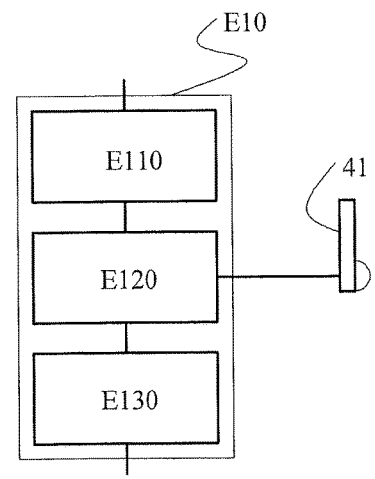

FIG. 6c is a diagram showing another embodiment of an acquisition method according to the invention. Apart from steps E10 to E30 described previously in relation to FIG. 6a, it comprises a step E50 of checking the exposure of a particular channel among a plurality of channels of the image acquired during said acquisition step E30, and a step E60 of selecting:

either said particular channel of the acquired image if the exposure of said image is judged to be correct at step E50, or another channel of the acquired image overexposed compared with said particular channel if the exposure of said image is judged to be underexposed at step E50, or another channel of the acquired image underexposed compared with said particular channel if the exposure of said image is judged to be overexposed at step E50.

In each of the embodiments that have just been described, the step E10 of measuring the transmission power of a finger an image of which is to be acquired is implemented by means of photoemitter 41 and photodetector 42, said step E10 comprising a first measuring substep E110, a substep of controlling the light intensity of said photoemitter 41 at:

a light intensity lower than the light intensity of substep E110 if the light intensity measured by the photodetector 42 is higher than a threshold intensity, a light intensity higher than the light intensity of substep E110 if the light intensity measured by the photodetector 42 is higher than a threshold intensity, and a new measuring step E130.

The invention claimed is:

1. An acquisition system comprising:
a camera designed to acquire an image of a finger when the finger is in front of the camera, a lighting device designed to illuminate said finger;
a control unit comprising a processor for controlling an intensity of illumination of said lighting device; and
at least one system for measuring a transmission power of said finger upstream of the camera with respect to the passage of said finger towards said camera,
the control unit being designed to control the illumination intensity of said lighting device according to the transmission power measured by said measuring system,
wherein the system is adapted to:

(1) check an exposure of the image acquired during the acquisition by the camera and adjust the illumination intensity of the lighting device if the exposure of said image is judged to be incorrect to:
- an illumination intensity lower than previous illumination intensity if the exposure of said image is judged to be overexposed, and
- an illumination intensity higher than the previous illumination intensity if the exposure of said image is judged to be underexposed, and/or, (2) check an exposure of a particular channel of the image acquired during the acquisition by the camera, and select:
- either said particular channel of the acquired image if the exposure of said image is judged to be correct, or
- another channel of the acquired image overexposed compared with said particular channel if the exposure of said image is judged to be underexposed,
- or another channel of the acquired image underexposed compared with said particular channel if the exposure of said image is judged to be overexposed, and/or, (3) measure the transmission power of the finger, the image of which is to be acquired, the acquisition system comprising a photoemitter and a photodetector, the acquisition system being adapted to control the light intensity of the photoemitter to:
- a light intensity lower than the light intensity of the measure if the light intensity measured by the photodetector is higher than a threshold intensity,
- a light intensity higher than the light intensity of the measure if the light intensity measured by the photodetector is higher than a threshold intensity, and perform a new measure.

2. The acquisition system according to claim 1, wherein said control unit functions in a learning mode for an elaboration and storage of a function linking the illumination intensity of said lighting device to said transmission power.

3. The acquisition system according to claim 1, wherein said control unit receives an image signal from said camera and is designed to complete an adjustment of the illumination intensity of said lighting device) by servocontrolling from one or more images acquired by means of said camera.

4. The acquisition system according to claim 1, wherein said camera is designed to deliver an image on a plurality of channels, a first channel being more sensitive than a second channel, which is itself more sensitive than a third channel, said control unit receiving one of said channels and being designed to control the intensity of illumination of said lighting device so that said one of said channels is exposed to an acceptable level, said acquisition system further comprising a selector controlled by said control unit in order to select a channel among said channels that is exposed to a certain level.

5. The acquisition system according to claim 1, further comprising two measuring systems comprising a photoemitter and a photodetector, the photoemitter of one being designed to emit at a higher light intensity than the other.

6. The acquisition system according to claim 1, wherein a photoemitter of said measuring system has its light intensity controlled by said control unit.

7. An acquisition method implemented by means of an acquisition system comprising a camera designed to acquire an image of a finger when the finger is in front of the camera and a lighting device for illuminating said finger, said method comprising:
- a step of adjusting an intensity of illumination of said lighting device;
- a step of acquisition of said image by said camera; and
- a step of measuring a transmission power of a finger implemented prior to the presentation of said finger in front of the camera,
- the step of adjusting said lighting device comprising controlling the illumination intensity of said lighting device according to the transmission power measured at the measuring step, wherein:

(1) the acquisition step comprises a step of checking an exposure of the image acquired during said acquisition step, a new step of adjusting the illumination intensity of said lighting device being implemented if the exposure of said image is judged to be incorrect to:
- an illumination intensity lower than previous illumination intensity if the exposure of said image is judged to be overexposed, and
- an illumination intensity higher than the previous illumination intensity if the exposure of said image is judged to be underexposed, and/or, (2) the acquisition method further comprises:
- a step of checking an exposure of a particular channel of the image acquired during the acquisition step, and
- a step of selecting:
  - either said particular channel of the acquired image if the exposure of said image is judged to be correct at the checking step, or
  - another channel of the acquired image overexposed compared with said particular channel if the exposure of said image is judged to be underexposed at the checking step,
  - or another channel of the acquired image underexposed compared with said particular channel if the exposure of said image is judged to be overexposed at the checking step, and/or, (3) the step of measuring the transmission power of the finger, the image of which is to be acquired, is implemented by means of a photoemitter and a photodetector, said measuring step comprising a first measuring substep, a substep of controlling the light intensity of said photoemitter to:
- a light intensity lower than the light intensity of the first measuring substep if the light intensity measured by the photodetector is higher than a threshold intensity,
- a light intensity higher than the light intensity of the first measuring substep if the light intensity measured by the photodetector is higher than a threshold intensity, and
- a new measuring step.

8. The acquisition method according to claim 7, wherein a function linking the illumination intensity of said lighting device to said transmission power is obtained by learning.

\* \* \* \* \*